US009226506B2

(12) United States Patent
Larelle et al.

(10) Patent No.: US 9,226,506 B2
(45) Date of Patent: Jan. 5, 2016

(54) METHODS OF WEED CONTROL IN CHICORY

(71) Applicant: Dow AgroSciences LLC, Indianapolis, IN (US)

(72) Inventors: Dominique Larelle, Le Tremblay sur Mauldre (FR); Xavier de Gaujac, Peymeinade (FR); Nathalie Blanchier, Anais (FR); Philippe Leroux, Beugny (FR); Richard K. Mann, Franklin, IN (US); Hilde Eelen, Ghent (BE); Stefaan Deconinck, Vlierzele (BE)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/496,547

(22) Filed: Sep. 25, 2014

(65) Prior Publication Data

US 2015/0087514 A1    Mar. 26, 2015

Related U.S. Application Data

(60) Provisional application No. 61/882,251, filed on Sep. 25, 2013.

(51) Int. Cl.
*A01N 43/64* (2006.01)
*A01N 47/10* (2006.01)
*A01N 43/90* (2006.01)
*A01N 33/18* (2006.01)

(52) U.S. Cl.
CPC ............... *A01N 43/90* (2013.01); *A01N 33/18* (2013.01)

(58) Field of Classification Search
None
See application file for complete search history.

(56) References Cited

U.S. PATENT DOCUMENTS

| 5,858,924 | A | 1/1999 | Johnson et al. |
| 7,314,849 | B2 | 1/2008 | Balko et al. |
| 7,432,227 | B2 | 10/2008 | Balko et al. |
| 8,680,010 | B2 * | 3/2014 | Mann ............................ 504/136 |
| 2006/0014641 | A1 | 1/2006 | Zaghmout |
| 2008/0234130 | A1 | 9/2008 | McCutchen et al. |
| 2010/0043095 | A1 | 2/2010 | Wei |
| 2011/0053772 | A1 | 3/2011 | Troppmann et al. |
| 2011/0190136 | A1 | 8/2011 | Hufnagl et al. |
| 2011/0200571 | A1 | 8/2011 | Bell et al. |
| 2012/0178626 | A1 | 7/2012 | Mann et al. |

FOREIGN PATENT DOCUMENTS

| DE | 102009001681 | 9/2010 |
| DE | 102009001728 | 9/2010 |
| DE | 102009001730 | 9/2010 |
| DE | 102009001732 | 9/2010 |
| WO | 2009003222 | 1/2009 |
| WO | 2010022251 | 2/2010 |
| WO | 2010046419 | 4/2010 |
| WO | 2011000498 | 1/2011 |
| WO | 2011076345 | 6/2011 |
| WO | 2011094219 | 8/2011 |
| WO | 2011145015 | 11/2011 |

OTHER PUBLICATIONS

Wikipedia—Definition of Chicory.*
Tomlin, C. D. S., Ed., The Pesticide Manual: A World Compendium, "Penoxsulam," 15th ed., BCPC: Alton, 2009, pp. 874-875.
Tomlin, C. D. S., Ed., The Pesticide Manual: A World Compendium, "Trisulfuron-methyl," 15th ed., BCPC: Alton, 2009, pp. 1175-1177.
Tomlin, C. D. S., Ed., The Pesticide Manual: A World Compendium, "Propyzamide," 15th ed., BCPC: Alton, 2009, pp. 960-961.
Tomlin, C. D. S., Ed., The Pesticide Manual: A World Compendium, "Benfluralin," 15th ed., BCPC: Alton, 2009, pp. 81-82.
Tomlin, C. D. S., Ed., The Pesticide Manual: A World Compendium, "Trifluralin," 15th ed., BCPC: Alton, 2009, pp. 1173-1175.
Tomlin, C. D. S., Ed., The Pesticide Manual: A World Compendium, "Isoxaben," 15th ed., BCPC: Alton, 2009, pp. 678-679.
Tomlin, C. D. S., Ed., The Pesticide Manual: A World Compendium, "Flumioxazin," 15th ed., BCPC: Alton, 2009, pp. 530-531.
International Search Report and Written Opinion issued Dec. 11, 2014, in International Patent Application No. PCT/US14/57428.
Farm Chemical International, Crop Protection Database, "Penoxsulam," available at http://www.farmchemicalsinternational.com/crop-protection-database/#/product/detail/424174/ (accessed on May 27, 2014).

* cited by examiner

*Primary Examiner* — Alton Pryor
(74) *Attorney, Agent, or Firm* — Michael R. Asam; Meunier Carlin & Curfman, LLC

(57) ABSTRACT

Disclosed herein are methods of controlling undesirable vegetation in chicory which can comprise applying to vegetation or an area adjacent the vegetation or applying to soil to prevent the emergence or growth of vegetation (a) penoxsulam or an agriculturally acceptable salt thereof. The methods can further comprise applying (b) a second pesticide or an agriculturally acceptable salt or ester thereof to the vegetation or the area adjacent the vegetation, or to the soil adjacent thereto. In some embodiments, (b) includes an ALS inhibitor (e.g., triflusulfuron-methyl), an inhibitor of microtubule assembly (e.g., propyzamide, trifluralin, or benfluralin), a cellulose biosynthesis inhibitor (e.g., isoxaben), a protoporphyrinogen oxidase (PPO) inhibitor (e.g., flumioxazin), or combinations thereof.

22 Claims, No Drawings

METHODS OF WEED CONTROL IN
CHICORY

CROSS REFERENCE TO RELATED APPLICATIONS

This application claims the benefit of U.S. Provisional Patent Application Ser. No. 61/882,251 filed Sep. 25, 2013, the disclosure of which is expressly incorporated herein by reference.

FIELD OF THE DISCLOSURE

The present disclosure also relates to methods for controlling undesirable vegetation in chicory (*Cichorium intybus*), whitloof chicory, and hybrids thereof.

BACKGROUND

Many recurring problems in agriculture involve controlling growth of undesirable vegetation that can, for instance, inhibit crop growth. To help control undesirable vegetation, researchers have produced a variety of chemicals and chemical formulations effective in controlling such unwanted growth. However, a continuing need exists for new compositions and methods to control growth of undesirable vegetation.

In particular, chicory is cultivated in multiple regions of the world, including the Netherlands, Belgium, France, Australia, and Chile. The control of unwanted vegetation in chicory takes place in the field, where the roots are produced (i.e., the root phase of the crop). Once produced, the chicory roots can be used for inulin production, as a coffee substitute, or to grow white Belgian endive leaves (i.e., the forcing phase of the crop), depending on the *Chicorium intybus* subspecies. Existing methods of controlling undesirable vegetation in chicory suffer from significant shortcomings. While pre-emergence and post-emergence treatments are both used to control weeds in chicory production, existing commercial herbicides typically cause significant injury to the chicory crop, resulting in reduced crop yields.

SUMMARY OF THE DISCLOSURE

Penoxsulam is a triazolopyrimidine sulfonamide herbicide which can be used to control broadleaf weeds in a variety of monocot crops, such as rice, winter cereals, corn/maize, sorghum, and turf, and dicot crops, such as perennial fruit and nut trees and vines. The present disclosure is based on the unexpected discovery that (a) penoxsulam or an agriculturally acceptable salt thereof can be applied to the broadleaf crop chicory to control undesirable vegetation without causing commercially unacceptable levels of crop damage.

Accordingly, the present disclosure relates to methods of controlling undesirable vegetation in chicory, which comprise applying to vegetation or an area adjacent the vegetation or applying to soil to prevent the emergence or growth of vegetation (a) penoxsulam or an agriculturally acceptable salt thereof. In some embodiments, (a) is applied in an amount of from 0.25 to 50 grams active ingredient per hectare (g ai/ha) (e.g., from 3 to 30 g ai/ha). Methods can involve applying (a) penoxsulam or an agriculturally acceptable salt thereof from 1 to 6 times per crop season.

The method can further comprise applying (b) a second pesticide or an agriculturally acceptable salt or ester thereof to the vegetation or the area adjacent the vegetation, or to the soil adjacent thereto. Pesticides (a) and (b) can be applied simultaneously or sequentially. Pesticides (a) and (b) can be applied in a single application or in multiple applications. In some embodiments, (b) includes an acetolactate synthase (ALS) inhibitor, an inhibitor of microtubule assembly, a cellulose biosynthesis inhibitor, a protoporphyrinogen (PPO) inhibitor, or combinations thereof. In some embodiments, (b) includes an acetolactate synthase (ALS) inhibitor, an inhibitor of microtubule assembly, or combinations thereof. In certain embodiments, (b) is selected from the group consisting of triflusulfuron-methyl, propyzamide, benfluralin, trifluralin, isoxaben, flumioxazin, and combinations thereof. In certain embodiments, (b) is selected from the group consisting of triflusulfuron-methyl, propyzamide, benfluralin, trifluralin, and combinations thereof.

Pesticides (a) and (b) can be applied in a weight ratio of (a) to (b) from 1:1000 to 10:1 (e.g., from 1:500 to 1:2). In some embodiments, (b) can be applied in an amount of from 2 to 2000 g ai/ha (e.g., from 20 to 1200 g ai/ha). In some embodiments, (a) is applied in an amount from 0.5 to 50 g ai/ha and (b) is applied in an amount of from 2.5 to 500 g ai/ha.

The undesirable vegetation can be a broadleaf weed, grass weed, sedge weed, or combinations thereof. In certain embodiments, the undesirable vegetation includes *Artemisia biennis, Capsella bursa-pastoris, Coronopus didymus, Galinsoga ciliata, Galinsoga parviflora, Matricaria chamomilla, Senecio vulgaris, Solanum nigrum, Sonchus* species, and combinations thereof. In some embodiments, (a) and (b), when present, are applied prior to the emergence of the undesirable vegetation (i.e., pre-emergence). In some embodiments, (a) and (b), when present, are applied after emergence of the undesirable vegetation.

The description below sets forth details of one or more embodiments of the present disclosure. Other features, objects, and advantages will be apparent from the description and from the claims.

DETAILED DESCRIPTION

The present disclosure relates to methods of controlling undesirable vegetation in chicory, which comprise applying to vegetation or an area adjacent the vegetation or applying to soil to prevent the emergence or growth of vegetation (a) penoxsulam or an agriculturally acceptable salt thereof.

"Chicory," as used herein, refers to plants of the genus *Cichorium*, including plants of the species *Cichorium endivia*, plants of the species *Cichorium intybus*, varieties thereof, and hybrids thereof. The term "chicory" includes plants of the species *Cichorium intybus*, including "wild improved" chicories, "Barbe de Capucin" chicories, "sugar loaf" chicories, "Chioggia" chicories, "cicorino" chicories, "Verona" chicories, "Catalonia" chicories, "Treviso" chicories, "Variegato di Castelfranco" chicories, "Witloof" chicories (e.g., "Brussels" chicory or "chicon" chicory), "Soncino" chicories, "red" chicories (e.g., radicchios), "Industrial" chicories (e.g., chicories intended for roasting and for sugars), "fodder" or "game" chicories, and hybrids thereof. The term "chicory" also includes plants of the species *Cichorium endivia*, including curly endive, also referred to as frisée (var. *crispum*), escarole, or broad-leaved endive (var. *latifolia*), and hybrids thereof. In certain cases, the chicory can comprise *Cichorium intybus* L. var. *sativum* (root chicory, such as *Cichorium intybus* L. var. *sativum* DC). In certain cases, the chicory can comprise *Cichorium intybus* L. var. *foliosum* (leaf chicory; such as *Cichorium intybus* L. var. *foliosum* Hegi).

The term "herbicide," as used herein, means an active ingredient that kills, controls, or otherwise adversely modifies the growth of vegetation. A "herbicidally effective amount" is an amount of an active ingredient that causes a "herbicidal effect," i.e., an adversely modifying effect and includes deviations from, for instance, natural development, killing, regulation, desiccation, and retardation. The terms "plants" and "vegetation" can include, for instance, germinant seeds, emerging seedlings, and established vegetation.

Penoxsulam

Methods of the present disclosure can involve applying penoxsulam (i.e., 2-(2,2-difluoroethoxy)-N-(5,8-dimethoxy [1,2,4]triazolo[1,5-c]pyrimidin-2-yl)-6-trifluoromethyl)benzenesulfonamide) or an agriculturally acceptable salt thereof. Penoxsulam, shown below, is a triazolopyrimidine sulfonamide herbicide that provides broad-spectrum control of many annual, biannual, and perennial weeds. Penoxsulam, as well as methods of preparing penoxsulam, are known in the art. See, for example, U.S. Pat. No. 5,858,924 to Loughner, et al.

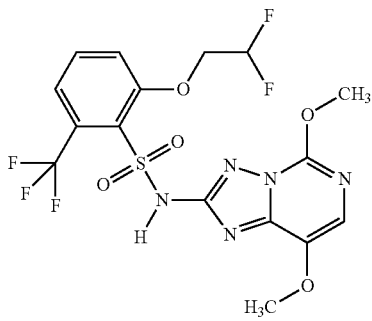 [SMILES: COc1cnc(OC)n2nc(NS(=O)(=O)c3c(OCC(F)F)cccc3C(F)(F)F)nc12]

In some embodiments, penoxsulam can be provided as an agriculturally acceptable salt of penoxsulam. Exemplary agriculturally acceptable salts of penoxsulam include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri (hydroxyethyl)ammonium, hydroxypropylammonium, di(hydroxypropyl)ammonium and tri(hydroxypropyl)ammonium salts, olamine salts, and diglycolamine salts.

Penoxsulam can be used to control broadleaf weeds in, for instance, rice, winter cereals, sorghum, corn, tree and vine crops, lawns (e.g., residential, industrial, and institutional), golf courses, parks, cemeteries, athletic fields, sod farms, range and pasture, rights-of-way, roadsides, and other crop and non-crop uses. Its herbicidal activity is described in Tomlin, C. D. S., Ed. *The Pesticide Manual: A World Compendium*, 15$^{th}$ ed.; BCPC: Alton, 2009 (hereafter "*The Pesticide Manual*, Fifteenth Edition, 2009"). Penoxsulam is or has been commercially available, for example, from Dow AgroSciences LLC under the trademarks VIPER®, BOA®, RAINBOW®, CLIPPER®, FENCER®, SAPPHIRE®, GRASP®, BENGALA®, and GRANITE®, and from SePRO Corporation under the trademark GALLEON®.

Penoxsulam or an agriculturally acceptable salt thereof can be applied to vegetation or an area adjacent the vegetation or applied to soil to prevent the emergence or growth of vegetation in an amount sufficient to induce a herbicidal effect. In certain embodiments, penoxsulam is applied in an amount sufficient to control undesirable vegetation in chicory without causing significant crop damage. In some embodiments, the penoxsulam or agriculturally acceptable salt thereof is applied to vegetation or an area adjacent the vegetation or applied to soil to prevent the emergence or growth of vegetation in an amount of 0.25 grams active ingredient per hectare (g ai/ha) or greater (e.g., 0.5 g ai/ha or greater, 1 g ai/ha or greater, 2 g ai/ha or greater, 1 g ai/ha or greater, 2 g ai/ha or greater, 3 g ai/ha or greater, 4 g ai/ha or greater, 5 g ai/ha or greater, 6 g ai/ha or greater, 7 g ai/ha or greater, 7.5 g ai/ha or greater, 8 g ai/ha or greater, 9 g ai/ha or greater, 10 g ai/ha or greater, 11 g ai/ha or greater, 12 g ai/ha or greater, 13 g ai/ha or greater, 14 g ai/ha or greater, 15 g ai/ha or greater, 16 g ai/ha or greater, 17 g ai/ha or greater, 18 g ai/ha or greater, 19 g ai/ha or greater, 20 g ai/ha or greater, 21 g ai/ha or greater, 22 g ai/ha or greater, 23 g ai/ha or greater, 24 g ai/ha or greater, 25 g ai/ha or greater, 26 g ai/ha or greater, 27 g ai/ha or greater, 28 g ai/ha or greater, 29 g ai/ha or greater, 30 g ai/ha or greater, 31 g ai/ha or greater, 32 g ai/ha or greater, 33 g ai/ha or greater, 34 g ai/ha or greater, 35 g ai/ha or greater, 36 g ai/ha or greater, 37 g ai/ha or greater, 38 g ai/ha or greater, 39 g ai/ha or greater, 40 g ai/ha or greater, 41 g ai/ha or greater, 42 g ai/ha or greater, 43 g ai/ha or greater, 44 g ai/ha or greater, 45 g ai/ha or greater, 46 g ai/ha or greater, 47 g ai/ha or greater, 48 g ai/ha or greater, or 49 g ai/ha or greater). In some embodiments, the penoxsulam or agriculturally acceptable salt thereof is applied to vegetation or an area adjacent the vegetation or applied to soil to prevent the emergence or growth of vegetation in an amount of 50 g ai/ha or less (e.g., 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9 g ai/ha or less, 8 g ai/ha or less, 7.5 g ai/ha or less, 7 g ai/ha or less, 6 g ai/ha or less, 5 g ai/ha or less, 4 g ai/ha or less, 3 g ai/ha or less, 2 g ai/ha or less, 1 g ai/ha or less, or 0.5 g ai/ha or less).

Penoxsulam can be applied to vegetation or an area adjacent the vegetation or applied to soil to prevent the emergence or growth of vegetation in an amount ranging from any of the minimum values described above to any of the maximum values described above. In some embodiments, the penoxsulam or agriculturally acceptable salt thereof is applied to vegetation or an area adjacent the vegetation or applied to soil to prevent the emergence or growth of vegetation in an amount of from 0.25 to 50 g ai/ha (e.g., from 1 to 45 g ai/ha, from 2 to 40 g ai/ha, or from 3 to 30 g ai/ha). Methods can involve applying (a) penoxsulam or an agriculturally acceptable salt thereof from 1 to 6 times per crop season.

The method described herein can further comprise applying (b) a second pesticide or an agriculturally acceptable salt or ester thereof to the vegetation or the area adjacent the vegetation, or to the soil adjacent thereto. In some embodiments, (b) includes an acetolactate synthase (ALS) inhibitor. Examples of ALS inhibitors include sulfonylureas, such as amidosulfuron, azimsulfuron, bensulfuron (e.g., bensulfuron-methyl), chlorimuron (e.g., chlorimuron-methyl), cinosulfuron, cyclosulfamuron, ethametsulfuron (e.g., ethametsulfuron-methyl), ethoxysulfuron, flazasulfuron, flupyrsulfuron (e.g., flupyrsulfuron-methyl sodium), foramsulfuron, halosulfuron (e.g., halosulfuron-methyl), imazosulfuron, iodosulfuron, iofensulfuron, mesosulfuron, metazosulfuron, metsulfuron (e.g., metsulfuron-methyl), nicosulfuron, orthosulfamuron, oxasulfuron, primisulfuron (e.g., primisulfuron-methyl), propyrisulfuron, prosulfuron, pyrazosulfuron (e.g., pyrazosulfuron-methyl), rimsulfuron, sulfometuron (e.g., sulfometuron-methyl), sulfosulfuron, thifensulfuron (e.g., thifensulfuron-methyl), triasulfuron, tribenuron (e.g., tribenuron-methyl), trifloxysulfuron, triflusulfuron (e.g., triflusulfuron-methyl), and tritosulfuron; sulfonanilides, such as pyrimisulfan and triafamone; imidazolinones, such as imazapic, imazamethabenz (e.g., imazamethabenz-methyl), imazamox, imazapyr, imazaquin, and imazethapyr; triazolopyrimidines, such as cloransulam (e.g., cloransulam-methyl), diclosulam, florasulam, flumetsulam, metosulam, and pyroxsulam; pyrimidinyl(thio)benzoates, such as bispyribac (e.g., bispyribac-sodium), pyribenzoxim, pyriftalid, pyrithiobac (e.g., pyrithiobac-sodium), and pyriminobac (e.g., pyriminobac-methyl); sulfonylaminocarbonyltriazolinones, such as flucarbazone (e.g., flucarbazone-sodium) and propoxycarbazone (e.g., propoxycarbazone-sodium); agriculturally acceptable salts and esters thereof; and combinations thereof. In some embodiments, (b) includes an inhibitor of microtubule assembly. Examples of inhibitors of microtubule assembly include dinitroanilines, such as benfluralin (also referred to as benefin), butralin, dinitramine, ethalfluralin, oryzalin, pendimethalin, and trifluralin; phosphoroamidates, such as amiprophos (e.g., amiprophos-methyl) and butamiphos; pyridines, such as dithiopyr and thiazopyr; benzamides, such as propyzamide (also referred to as pronamide); benzoic acids, such as chlorthal (e.g., chlorthal-dimethyl); agriculturally acceptable salts and esters thereof; and combinations thereof. In some embodiments, (b) includes a cellulose biosynthesis inhibitor. Examples of cellulose biosynthesis inhibitors include nitriles, such as chlorthiamid and dichlobenil; benzamides, such as isoxaben; alkylazines, such as triaziflam and indaziflam; triazolocarboxamides, such as fluopoxam; agriculturally acceptable salts and esters thereof; and combinations thereof. In some embodiments, (b) includes a protoporphyrinogen oxidase (PPO) inhibitor. Examples of PPO inhibitors include diphenyl ethers, such as acifluorfen (e.g., acifluorfen-sodium), bifenox, chlomethoxyfen, ethoxyfen (e.g., ethoxyfen-ethyl), fluoroglycofen (e.g., fluoroglycofen-ethyl), fomesafen, halosafen, lactofen, and oxyfluorfen; thiadiazoles, such as fluthiacet (e.g., fluthiacet-methyl) and thidiazimin; pyrimidinediones, such as benzfendizone, butafenacil, and saflufenacil; oxadiazoles, such as oxadiargyl and oxadiazon; oxazolidinediones, such as pentoxazone; N-phenyl-phthalimides, such as cinidon (e.g., cinidon-ethyl), flumiclorac (e.g., flumiclorac-pentyl), and flumioxazin; phenylpyrazoles, such as fluazolate and pyraflufen (e.g., pyraflufen-ethyl); triazolinones, such as azafenidin, bencarbazone, carfentrazone (e.g., carfentrazone-ethyl), and sulfentrazone; others, such as flufenpyr (e.g., flufenpyr-ethyl), pyraclonil, and profluazol; agriculturally acceptable salts and esters thereof; and combinations thereof.

In certain embodiments, (b) can be selected from the group consisting of triflusulfuron-methyl, propyzamide, benfluralin, trifluralin, isoxaben, flumioxazin, and combinations thereof. In certain embodiments, (b) can be selected from the group consisting of triflusulfuron-methyl, propyzamide, benfluralin, trifluralin, and combinations thereof.

Triflusulfuron

Methods of the present disclosure can involve applying triflusulfuron or an agriculturally acceptable salt or ester thereof (e.g., triflusulfuron-methyl) in combination with penoxsulam for control of undesirable vegetation in chicory. Triflusulfuron (i.e., 2-[4-dimethylamino-6-(2,2,2-trifluoroethoxy)-1,3,5-triazin-2-ylcarbamoylsulfamoyl]-m-toluic acid) is a sulfonylurea herbicide that inhibits acetolactate synthase or ALS (i.e., an ALS inhibitor). Triflusulfuron (e.g., triflusulfuron-methyl) can be used to control annual grasses and broadleaf weeds, for instance, in sugar beets. Its herbicidal activity is described in *The Pesticide Manual*, Fifteenth Edition, 2009.

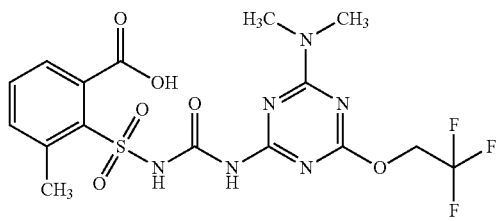 [SMILES: Cc1cccc(C(=O)O)c1S(=O)(=O)NC(=O)Nc1nc(OCC(F)(F)F)nc(N(C)C)n1]

Triflusulfuron can be provided in its acid form (as shown above) or as an agriculturally acceptable salt or ester thereof. Exemplary agriculturally acceptable salts of triflusulfuron include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts. In certain embodiments, triflusulfuron is provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters, and aryl esters such as benzyl. An exemplary agriculturally acceptable ester of triflusulfuron can include triflusulfuron-methyl.

Triflusulfuron or agriculturally acceptable salts or esters thereof are or have been commercially available, for example, under the trademarks UPBEET® and SAFARI® (by DuPont Crop Protection), SAVANA® (by Stockton Agrimor AG), and EFFECT® and WILLURON® (by Willowood Ltd.).

Propyzamide

Methods of the present disclosure can involve applying propyzamide or an agriculturally acceptable salt thereof. Propyzamide (i.e., 3,5-dichloro-N-(2-methylbut-3-yn-2-yl)benzamide) is a benzamide herbicide that inhibits microtubule assembly. Propyzamide can be used to control annual grasses and broadleaf weeds, for instance, in artichoke, endive, escarole, legumes, lettuce, rhubarb, sugar beets, blackberries, blueberries, boysenberries, raspberries, tree fruit, woody ornamentals, nursery stock, Christmas trees, Bermuda turf, fallow land, and gladiolus. Its herbicidal activity is described in *The Pesticide Manual*, Fifteenth Edition, 2009.

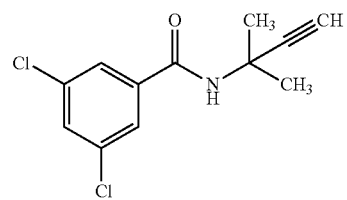 [SMILES: C#CC(C)(C)NC(=O)c1cc(Cl)cc(Cl)c1]

Propyzamide can be provided as an agriculturally acceptable salt of propyzamide. Exemplary agriculturally acceptable salts of propyzamide include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts.

Propyzamide or agriculturally acceptable salts thereof are or have been commercially available, for example, under the trademarks SETANTA®, SETANTA FLO®, and SOLITAIRE® (by AgriGuard Ltd.), KERB® (by Dow AgroSciences LLC), FERNAMIDE® (by Fertiagro Pte. Ltd.), PILARMAXI® (by Pilar AgriScience Corp.), SUNPYZAMIDE® (by Sundat Pte. Ltd.), WILLOWOOD PRONAMIDE® (by Willowood USA), KERNEL® (by SAFA TARIM A.S.), WOPRO-PROPYZAMIDE® (by B.V. Industrie- & Handelsonderneming Simonis), PONAMIDE® (by Willowood Ltd.), and POLKA® (by Zelam Ltd.).

Benfluralin

Methods of the present disclosure can involve applying benfluralin or an agriculturally acceptable salt thereof. Benfluralin (i.e., N-butyl-N-ethyl-2,6-dinitro-4-(trifluoromethyl)aniline) is a dinitroaniline herbicide that inhibits microtubule assembly. Benfluralin can be used to control annual grasses and broadleaf weeds, for instance, in seeded alfalfa, birdsfoot trefoil, clover (ladino, red), direct-seeded lettuce, peanuts, transplant air-cured (burley, dark) tobacco, and established turf. Its herbicidal activity is described in *The Pesticide Manual*, Fifteenth Edition, 2009.

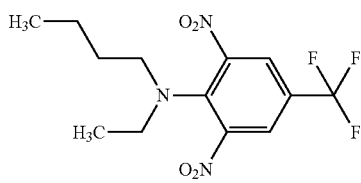 [SMILES: CCCCN(CC)c1c([N+](=O)[O-])cc(C(F)(F)F)cc1[N+](=O)[O-]]

Benfluralin can be provided as an agriculturally acceptable salt of benfluralin. Benfluralin or agriculturally acceptable salts thereof are or have been commercially available, for example, under the trademarks BONALAN® and QUILAN® (by Dow AgroSciences LLC), BENEFEX® (by Adama Agricultural Solutions, formerly Makhteshim Agan Group), and BALAN® (by Loveland Products, Inc.).

Trifluralin

Methods of the present disclosure can involve applying trifluralin or an agriculturally acceptable salt thereof. Trifluralin (i.e., 2,6-dinitro-N,N-dipropyl-4-(trifluoromethyl)aniline) is a dinitroaniline herbicide that inhibits microtubule assembly. Trifluralin can be used to control annual grasses and broadleaf weeds, for instance, in alfalfa, almonds, apricots, asparagus, barley, beans, broccoli, brussels sprouts, cabbage, cantaloupes, carrots, cauliflower, celery, collard, corn, cotton, cucumbers, grain sorghum, grapefruit, grapevines, hops, kale, lemons, nectarines, okra, oranges, peaches, peanuts, peas, pecans, peppers, plums, potatoes, prunes, soybeans, sugar beets, sugarcane, sunflowers, tangerines, tomatoes, turnip greens, walnuts, watermelon, and wheat. Its herbicidal activity is described in *The Pesticide Manual*, Fifteenth Edition, 2009.

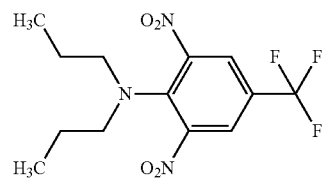

Trifluralin can be provided as an agriculturally acceptable salt of trifluralin. Trifluralin or agriculturally acceptable salts thereof are or have been commercially available, for example, under the trademarks SARCLINE® (by Agriphar S.A.), TRIVERDAX® (by Atanor S.C.A.), TREFLAN® (by Dow AgroSciences LLC), TEFRALIN® (by Hektas Ticaret T.A.S.), BAYONET® (by Helena Chemical Co.), EFLURIN® (by K & N. Efthymiadis S.A.), TIRIFILIN® (by Koruma Tarim A.S.), TREMOR® (by M/S Modern Insecticides Ltd.), TRIFLUREX® and PREMERLIN® (by Adama Agricultural Solutions, formerly Makhteshim Agan Group), TRIFLURALINA®, MILENIA®, and PREMERLIN® (by Milenia Agrociencias S.A.), PILARCHOICE® (by Pilar AgriScience Corp.), TRETOX 480® (by Pyosa, S.A. de C.V.), MEGA TREF® and TIRALIN® (by SAFA TARIM A.S.), GENO-TREF® (by Agri Sciences Co., Ltd.), ARCHER® (by Agroquimicos Versa, S.A. de C.V.), SUPER T® and TRI-4® (by BASF Corporation), TRIGERMIN® (by Chemiplant S.A.), FLURAN® (by Insecticidas Internacionales, C.A.), DIGERMIN® (by ISAGRO S.p.A.), LINEX® (by Ivorychem Pte. Ltd.), TRIFLULIN® (by Ladda Co., Ltd.), TRIFLUMAC® (by Medmac for Manufacturing Agricultural Chemicals & Veterinary Products Ltd.), TREFOR® (by Polsas Chemicals and Machinery Co.), WOPRO-TRIFLURALIN® (by B.V. Industrie- & Handelsondememing Simonis), TRIFLUSAN® (by Stockton Agrimor AG), TRAFAN® (by Tratamientos Guadalquivir S.L.), FLORA® (by United Phosphorus Ltd.), HERBIFLURIN® (by Veterinary & Agricultural Products Mfg. Co. Ltd.), RIFLE® (by Villa Crop Protection), and TRUST® (by Winfield Solutions, LLC).

Isoxaben

Methods of the present disclosure can involve applying isoxaben or an agriculturally acceptable salt thereof. Isoxaben (i.e., N-[3-(1-ethyl-1-methylpropyl)isoxazol-5-yl]-2,6-dimethoxybenzamide) is a benzamide herbicide that inhibits cellulose biosynthesis. Isoxaben can be used pre-emergence to control a broad-spectrum of autumn- and spring-germinating broadleaf weeds in winter and spring cereals, turf, fruit, berries, onions, garlic, vines, forestry, ornamental trees and shrubs, and non-bearing fruit and nut trees. Its herbicidal activity is described in *The Pesticide Manual*, Fifteenth Edition, 2009.

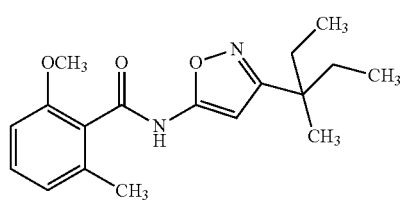 [SMILES: CCC(C)(CC)c1cc(NC(=O)c2c(C)cccc2OC)on1]

Isoxaben can be provided as an agriculturally acceptable salt of isoxaben. Exemplary agriculturally acceptable salts of isoxaben include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts.

Isoxaben or agriculturally acceptable salts thereof are or have been commercially available, for example, under the trademarks AZ 500®, GALLERY®, TRELLIS®, FLEXIDOR® 125, ROKENYL® 50, and Cent-7™ (by Dow AgroSciences LLC) and Isoxaben 75WG (by Quali-Pro).

Flumioxazin

Methods of the present disclosure can involve applying flumioxazin or an agriculturally acceptable salt thereof. Flumioxazin (i.e., N-(7-fluoro-3,4-dihydro-3-oxo-4-prop-2-ynyl-2H-1,4-benzoxazin-6-yl)cyclohex-1-ene-1,2-dicarboxamide) is a N-phenylphthalimide herbicide that inhibits protoporphyrinogen oxidase (PPO). Flumioxazin can be used for pre-emergence control of many annual broadleaf weeds and some annual grasses in soybeans, peanuts, orchards, vines, and other crops. Its herbicidal activity is described in *The Pesticide Manual*, Fifteenth Edition, 2009.

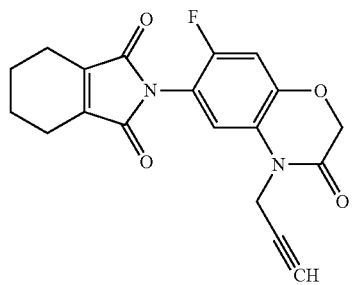 [SMILES: C#CCN1C(=O)COc2cc(F)c(N3C(=O)C4=C(CCCC4)C3=O)cc21]

Flumioxazin can be provided as an agriculturally acceptable salt of flumioxazin. Flumioxazin or agriculturally acceptable salts thereof are or have been commercially available, for example, under the trademarks BroadStar®, CHATEAU®, CLIPPER®, SureGuard®, VALOR®, and PAYLOAD® (by Valent U.S.A. Corporation), FLUMYZIN® (by Planet Aagro), SumiMax®, PLEDGE® 500, and SUMISOYA® (by Sumitomo Chemical Co. Ltd.) and VALTERA™ (by Valent Canada).

The second pesticide (b) or an agriculturally acceptable salt or ester thereof can be applied to vegetation or an area adjacent the vegetation or applied to soil to prevent the emergence or growth of vegetation in an amount sufficient to induce a herbicidal effect. In certain embodiments, (b) or an agriculturally acceptable salt or ester thereof is applied in an amount sufficient to control undesirable vegetation in chicory without causing significant crop damage. In some embodiments, the (b) or agriculturally acceptable salt or ester thereof is applied to vegetation or an area adjacent the vegetation or applied to soil to prevent the emergence or growth of vegetation in an amount of 2 grams active ingredient per hectare (g ai/ha) or greater (e.g., 5 g ai/ha or greater, 10 g ai/ha or greater, 15 g ai/ha or greater, 20 g ai/ha or greater, 25 g ai/ha or greater, 30 g ai/ha or greater, 35 g ai/ha or greater, 40 g ai/ha or greater, 45 g ai/ha or greater, 50 g ai/ha or greater, 60 g ai/ha or greater, 70 g ai/ha or greater, 75 g ai/ha or greater, 80 g ai/ha or greater, 90 g ai/ha or greater, 100 g ai/ha or greater, 150 g ai/ha or greater, 200 g ai/ha or greater, 250 g ai/ha or greater, 300 g ai/ha or greater, 350 g ai/ha or greater, 400 g ai/ha or greater, 450 g ai/ha or greater, 500 g ai/ha or greater, 550 g ai/ha or greater, 600 g ai/ha or greater, 650 g ai/ha or greater, 700 g ai/ha or greater, 750 g ai/ha or greater, 800 g ai/ha or greater, 850 g ai/ha or greater, 900 g ai/ha or greater, 950 g ai/ha or greater, 1000 g ai/ha or greater, 1050 g ai/ha or greater, 1100 g ai/ha or greater, 1150 g ai/ha or greater, 1200 g ai/ha or greater, 1250 g ai/ha or greater, 1300 g ai/ha or greater, 1350 g ai/ha or greater, 1400 g ai/ha or greater, 1450 g ai/ha or greater, 1500 g ai/ha or greater, 1550 g ai/ha or greater, 1600 g ai/ha or greater, 1650 g ai/ha or greater, 1700 g ai/ha or greater, 1750 g ai/ha or greater, 1800 g ai/ha or greater, 1850 g ai/ha or greater, 1900 g ai/ha or greater, or 1950 g ai/ha or greater). In some embodiments, the (b) or agriculturally acceptable salt or ester thereof is applied to vegetation or an area adjacent the vegetation or applied to soil to prevent the emergence or growth of vegetation in an amount of 2000 g ai/ha or less (e.g., 1950 g ai/ha or less, 1900 g ai/ha or less, 1850 g ai/ha or less, 1800 g ai/ha or less, 1750 g ai/ha or less, 1700 g ai/ha or less, 1650 g ai/ha or less, 1600 g ai/ha or less, 1550 g ai/ha or less, 1500 g ai/ha or less, 1450 g ai/ha or less, 1400 g ai/ha or less, 1350 g ai/ha or less, 1300 g ai/ha or less, 1250 g ai/ha or less, 1200 g ai/ha or less, 1150 g ai/ha or less, 1100 g ai/ha or less, 1050 g ai/ha or less, 1000 g ai/ha or less, 950 g ai/ha or less, 900 g ai/ha or less, 850 g ai/ha or less, 800 g ai/ha or less, 750 g ai/ha or less, 700 g ai/ha or less, 650 g ai/ha or less, 600 g ai/ha or less, 550 g ai/ha or less, 500 g ai/ha or less, 450 g ai/ha or less, 400 g ai/ha or less, 350 g ai/ha or less, 300 g ai/ha or less, 250 g ai/ha or less, 200 g ai/ha or less, 150 g ai/ha or less, 100 g ai/ha or less, 90 g ai/ha or less, 80 g ai/ha or less, 75 g ai/ha or less, 70 g ai/ha or less, 60 g ai/ha or less, 50 g ai/ha or less, 45 g ai/ha or less, 40 g ai/ha or less, 35 g ai/ha or less, 30 g ai/ha or less, 25 g ai/ha or less, 20 g ai/ha or less, 15 g ai/ha or less, 10 g ai/ha or less, or 5 g ai/ha or less).

The second pesticide (b) or an agriculturally acceptable salt or ester thereof can be applied to vegetation or an area adjacent the vegetation or applied to soil to prevent the emergence or growth of vegetation in an amount ranging from any of the minimum values described above to any of the maximum values described above. In some embodiments, the (b) or agriculturally acceptable salt or ester thereof is applied to vegetation or an area adjacent the vegetation or applied to soil to prevent the emergence or growth of vegetation in an amount of from 2 to 2000 g ai/ha (e.g., from 20 to 1200 g ai/ha, from 1 to 500 g ai/ha, from 5 to 400 g ai/ha, from 10 to 300 g ai/ha, from 15 to 250 g ai/ha, or from 20 to 200 g ai/ha).

In some embodiments, (a) penoxsulam or an agriculturally acceptable salt thereof is the sole pesticide applied to control undesirable vegetation in chicory. In other embodiments, methods of controlling undesirable vegetation in chicory comprise applying to vegetation or an area adjacent the vegetation or applying to soil to prevent the emergence or growth of vegetation (a) penoxsulam or an agriculturally acceptable salt thereof and (b) a second pesticide selected from an acetolactate synthase (ALS) inhibitor, an inhibitor of microtubule assembly, a cellulose biosynthesis inhibitor, a protoporphyrinogen oxidase (PPO) inhibitor, or combinations thereof. In some embodiments, methods of controlling undesirable vegetation in chicory comprise applying to vegetation or an area adjacent the vegetation or applying to soil to prevent the emergence or growth of vegetation (a) penoxsulam or an agriculturally acceptable salt thereof and (b) a second pesticide selected from an acetolactate synthase (ALS) inhibitor, an inhibitor of microtubule assembly, or combinations thereof. In some embodiments, (b) can be selected from the group consisting of triflusulfuron-methyl, propyzamide, benfluralin, trifluralin, isoxaben, flumioxazin, and combinations thereof. In certain embodiments, (b) can be selected from the group consisting of triflusulfuron-methyl, propyzamide, benfluralin, trifluralin, and combinations thereof.

In some embodiments, the weight ratio of (a) penoxsulam or agriculturally acceptable salt thereof to (b) a second pesticide (e.g., triflusulfuron, propyzamide, benfluralin, trifluralin, isoxaben, flumioxazin, or combinations thereof) or an agriculturally acceptable salt or ester thereof that is applied to control undesirable vegetation in chicory is at least 1:1000 (e.g., at least 1:900, at least 1:800, at least 1:700, at least 1:600, at least 1:500, at least 1:400, at least 1:300, at least 1:200, at least 1:100, at least 1:90, at least 1:80, at least 1:70, at least 1:60, at least 1:50, at least 1:40, at least 1:30, at least 1:20, at least 1:10, at least 1:8, at least 1:6, at least 1:5, at least 1:4, at least 1:2, at least 1:1, at least 2:1, at least 4:1, at least 5:1, at least 6:1, or at least 8:1). In some embodiments, the weight ratio of (a) to (b) that is applied to control undesirable vegetation in chicory is 10:1 or less (e.g., 8:1 or less, 6:1 or less, 5:1 or less, 4:1 or less, 2:1 or less, 1:1 or less, 1:2 or less, 1:4 or less, 1:5 or less, 1:6 or less, 1:8 or less, 1:10 or less, 1:20 or less, 1:30 or less, 1:40 or less, 1:50 or less, 1:60 or less, 1:70 or less, 1:80 or less, 1:90 or less, 1:100 or less, 1:200 or less, 1:300 or less, 1:400 or less, 1:500 or less, 1:600 or less, 1:700 or less, 1:800 or less, or 1:900 or less).

The weight ratio of (a) penoxsulam or agriculturally acceptable salt thereof to (b) a second pesticide or an agriculturally acceptable salt or ester thereof that is applied to control undesirable vegetation in chicory can range from any of the minimum ratios described above to any of the maximum values described above. In some embodiments, the weight ratio of (a) penoxsulam or agriculturally acceptable salt thereof to (b) a second pesticide or an agriculturally acceptable salt or ester thereof that is applied to control undesirable vegetation in chicory is from 1:1000 to 10:1 (e.g., from 1:500 to 8:1, from 1:200 to 6:1, from 1:100 to 5:1, from 1:50 to 2:1, from 1:25 to 1:1, from 1:8 to 1:1, from 1:8 to 1:4, from 1:500 to 1:2, or from 1:300 to 1:30).

Formulations

The present disclosure also relates to formulations for use in conjunction with the methods disclosed herein.

In some embodiments, the formulation can be in the form of a single package formulation including (a) penoxsulam or an agriculturally acceptable salt thereof and optionally (b) a second pesticide or an agriculturally acceptable salt or ester thereof. In some embodiments, the formulation can be in the form of a single package formulation including both (a) and (b) and further including at least one additive. In some embodiments, the formulation can be in the form of a two-package formulation, wherein one package contains (a) and optionally at least one additive while the other package contains (b) and optionally at least one additive. In some embodiments of the two-package formulation, the formulation including (a) and optionally at least one additive and the formulation including (b) and optionally at least one additive are mixed before application and then applied simultaneously. In some embodiments, the mixing is performed as a tank mix (i.e., the formulations are mixed immediately before or upon dilution with water). In some embodiments, the formulation including (a) and the formulation including (b) are not mixed but are applied sequentially (in succession), for example, immediately or within 1 hour, within 2 hours, within 4 hours, within 8 hours, within 16 hours, within 24 hours, within 2 days, or within 3 days, of each other.

In some embodiments, the formulation of (a) and/or (b) is present in suspended, emulsified, or dissolved form. Exemplary formulations include, but are not limited to, aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, and materials for spreading or granules.

In some embodiments, (a) penoxsulam or an agriculturally acceptable salt thereof and/or (b) a second pesticide or an agriculturally acceptable salt or ester thereof is an aqueous solution that can be diluted before use. In some embodiments, (a) and/or (b) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of −10° C. or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

In some embodiments, (a) penoxsulam or an agriculturally acceptable salt thereof is provided in a premixed formulation with an acetolactate synthase (ALS) inhibitor, an inhibitor of microtubule assembly, a cellulose biosynthesis inhibitor, a protoporphyrinogen oxidase (PPO) inhibitor, or combinations thereof (e.g., triflusulfuron-methyl, propyzamide, benfluralin, trifluralin, isoxaben, flumioxazin, or combinations thereof).

In some embodiments, (a) penoxsulam or an agriculturally acceptable salt thereof and/or (b) a second pesticide or an agriculturally acceptable salt or ester thereof can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the penoxsulam or agriculturally acceptable salt thereof. In some embodiments, the additive is premixed with the second pesticide or agriculturally acceptable salt or ester thereof. In some embodiments, the additive is premixed with the penoxsulam or agriculturally acceptable salt thereof and the second pesticide or agriculturally acceptable salt or ester thereof.

In some embodiments, the additive is an additional pesticide. Exemplary additional pesticides include, but are not limited to, 2,4-D, acetochlor, aclonifen, amicarbazone, 4-aminopicolinic acid based herbicides, such as halauxifen, halauxifen-methyl, benzyl 4-amino-3-chloro-6-(4-chloro-2-fluoro-3-methoxyphenyl)-5-fluoropicolinate, 4-amino-3-chloro-6-(4-chloro-2-fluoro-3-methoxyphenyl)-5-fluoropicolinic acid or agriculturally acceptable salts or esters thereof, and those described in U.S. Pat. Nos. 7,314,849 and 7,432,227 to Balko, et al., amidosulfuron, aminocyclopyrachlor, aminopyralid, aminotriazole, ammonium thiocyanate, asulam, atrazine, beflubutamid, benazolin, bensulfuron-methyl, bentazone, bifenox, bromacil, bromoxynil, butachlor, butafenacil, butralin, butroxydim, carbetamide, carfentrazone, carfentrazone-ethyl, chlormequat, clopyralid, chlorsulfuron, chlortoluron, cinidon-ethyl, clethodim, clodinafop-propargyl, clomazone, cyanazine, cyclosulfamuron, cycloxydim, cyhalofop, cyhalofop-butyl, dicamba, dichlobenil, dichlorprop-P, diclofop-methyl, diclosulam, diflufenican, diflufenzopyr, dimefuron, dimethachlor, diquat, diuron, S-ethyl dipropylcarbamothioate (EPTC), ethoxysulfuron, fenoxaprop, fenoxaprop-ethyl, fenoxaprop-ethyl+isoxadifen-ethyl, fenoxaprop-P-ethyl, fenoxasulfone, flazasulfuron, florasulam, fluazifop, fluazifop-P-butyl, flucarbazone, flucarbazone-sodium, flucetosulfuron (LGC-42153), flufenacet, flumetsulam, flumioxazin, flupyrsulfuron, flurochloridone, fluroxypyr, fluroxypyr-meptyl, flurtamone, glufosinate, glufosinate-ammonium, glyphosate, haloxyfop, haloxyfop-methyl, hexazinone, imazamethabenz, imazamox, imazapic, imazapyr, imazaquin, imazethapyr, imazosulfuron, indanofan, indaziflam, iodosulfuron, iodosulfuron-ethyl-sodium, ioxynil, isoproturon, isoxaben, isoxaflutole, lactofen, linuron, MCPA, MCPB, mecoprop-P, mesosulfuron, mesosulfuron-ethyl sodium, metazochlor, metosulam, metribuzin, metsulfuron, metsulfuron-methyl, MSMA, napropamide, napropamide-M, norfurazon, orthosulfamuron, oryzalin, oxadiargyl, oxadiazon, oxyfluorfen, paraquat, pendimethalin, picloram, picolinafen, pinoxaden, primisulfuron, profluazol, propaquizafop, propoxycarbazone, prosulfocarb, prosulfuron, pyraflufen-ethyl, pyrasulfotole, pyribenzoxim (LGC-40863), pyroxsulam, pyroxasulfone, quinmerac, quizalofop-ethyl-D, quizalofop-P-ethyl, quizalofop-P-tefuryl, rimsulfuron, saflufenacil, sethoxydim, simazine, sulfentrazone, sulfometuron, sulfosate, sulfosulfuron, tebuthiuron, tepraloxidim, terbacil, terbuthylazine, terbutryn, thiazopyr, thifensulfuron, thifensulfuron-methyl, topramezone, tralkoxydim, triasulfuron, tribenuron, tribenuron-methyl, triafamone, triclopyr, and agriculturally acceptable salts, esters and mixtures thereof.

In some embodiments, the penoxsulam or an agriculturally acceptable salt thereof is provided in a premixed formulation with an additional pesticide. In some embodiments, the penoxsulam or an agriculturally acceptable salt thereof is premixed with cyhalofop-butyl, oxyfluorfen, triclopyr, or combinations thereof. Exemplary premixes of penoxsulam or an agriculturally acceptable salt thereof and an additive that are or have been commercially available include, but are not limited to, TOP SHOT® (a premix incorporating cyhalofop-butyl by Dow AgroSciences LLC), REBEL EX® (a premix incorporating cyhalofop-butyl by Dow AgroSciences LLC), PINDAR® GT (a premix incorporating oxyfluorfen by Dow AgroSciences LLC) and GRASP® XTRA (a premix incorporating triclopyr by Dow AgroSciences LLC).

In some embodiments, the second pesticide or an agriculturally acceptable salt or ester thereof is provided in a premixed formulation with an additional pesticide. In some embodiments, the second pesticide is benfluralin or an agriculturally acceptable salt thereof that is provided in a premixed formulation with an additional pesticide. In some embodiments, the benfluralin or an agriculturally acceptable salt thereof is premixed with oryzalin, trifluralin, or combinations thereof. Exemplary premixes of benfluralin or an agriculturally acceptable salt thereof and an additive that are or have been commercially available include, but are not limited to, SURFLAN XL® (a premix incorporating oryzalin by United Phosphorus, Inc.); XL 2G® (a premix incorporating oryzalin by Helena Chemical Co.); and TEAM® (a premix incorporating trifluralin by Dow AgroSciences LLC).

In some embodiments, the second pesticide or an agriculturally acceptable salt or ester thereof is provided in a premixed formulation with an additional pesticide. In some embodiments, the second pesticide is trifluralin or an agriculturally acceptable salt thereof that is provided in a premixed formulation with an additional pesticide. In some embodiments, the trifluralin or an agriculturally acceptable salt thereof is premixed with benfluralin, clodinafop-propargyl, fluometuron, imazaquin, imazethapyr, isoxaben, oxyfluorfen, linuron, oryzalin, pendimethalin, or combinations thereof. Exemplary premixes of trifluralin or an agriculturally acceptable salt thereof and an additive that are or have been commercially available include, but are not limited to, TEAM® (a premix incorporating benfluralin by Dow AgroSciences LLC); HAWK® and RESERVE® (premixes incorporating clodinafop-propargyl by Syngenta); COTOLINA® (a premix incorporating fluometuron by Aragonesas Agro, S.A.); COTTONEX COMBI® (a premix incorporating fluometuron by Makhteshim Agan Group); TRI-SCEPT® (a premix incorporating imazaquin by BASF Corporation); PASSPORT® (a premix incorporating imazethapyr by BASF Corporation); SNAPSHOT 2.5 TG® (a premix incorporating isoxaben by Dow AgroSciences LLC); SHOWCASE® (a premix incorporating isoxaben and oxyfluorfen by Dow AgroSciences LLC); ARIZONA®, BLOIS®, LINNET®, and URANUS® (premixes incorporating linuron by Makhteshim Agan Group); YIELD® (a premix incorporating oryzalin by United Phosphorus Ltd.); and SWORD® and ZIMBALI® (premixes incorporating pendimethalin by Makhteshim Agan Group).

In some embodiments, the second pesticide or an agriculturally acceptable salt or ester thereof is provided in a premixed formulation with an additional pesticide. In some embodiments, the second pesticide is isoxaben or an agriculturally acceptable salt thereof that is provided in a premixed formulation with an additional pesticide. In some embodiments, the isoxaben or an agriculturally acceptable salt thereof is premixed with chlorotoluron, trifluralin, oxyfluorfen, oryzalin, florasulm, or combinations thereof. Exemplary premixes of isoxaben or an agriculturally acceptable salt thereof and an additive that are or have been commercially available include, but are not limited to, AUBAINE® (a premix incorporating chlorotoluron by Dow AgroSciences LLC); SNAPSHOT 2.5 TG® and ELSET TF® (premixes incorporating trifluralin by Dow AgroSciences LLC); SHOWCASE® (a premix incorporating trifluralin and oxyfluorfen by Dow AgroSciences LLC); WINCHED (a premix incorporating oryzalin by Dow AgroSciences LLC); ALUR®, ASAP®, HAUBAN®, and X-Pand®(premixes incorporating florasulam by Dow AgroSciences LLC).

In some embodiments, the second pesticide or an agriculturally acceptable salt or ester thereof is provided in a premixed formulation with an additional pesticide. In some embodiments, the second pesticide is flumioxazin or an agriculturally acceptable salt thereof that is provided in a premixed formulation with an additional pesticide. In some embodiments, the flumioxazin or an agriculturally acceptable salt thereof is premixed with pyroxasulfone or combinations thereof. Exemplary premixes of flumioxazin or an agriculturally acceptable salt thereof and an additive that are or have been commercially available include, but are not limited to, FIERCE® (a premix incorporating pyroxasulfone by Valent Canada).

In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+emulsifiers (15%)) or less, nonylphenol ethoxylate or less, benzylcocoalkyldimethyl quaternary ammonium salt or less, blend of petroleum hydrocarbon, alkyl esters, organic acid, and anionic surfactant or less, $C_9$-$C_{11}$ alkylpolyglycoside or less, phosphate alcohol ethoxylate or less, natural primary alcohol ($C_{12}$-$C_{16}$) ethoxylate or less, di-sec-butylphenol EO-PO block copolymer or less, polysiloxane-methyl cap or less, nonylphenol ethoxylate+urea ammonium nitrate or less, emulsified methylated seed oil or less, tridecyl alcohol (synthetic) ethoxylate (8 EO) or less, tallow amine ethoxylate (15 EO) or less, and PEG (400) dioleate-99.

In some embodiments, the additive is a safener that is an organic compound leading to better crop plant compatibility when applied with a herbicide. In some embodiments, the safener itself is herbicidally active. In some, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet (mexyl), cyometrinil, cyprosulfamide, daimuron, dichlormid, dicyclonon, dietholate, dimepiperate, disulfoton, fenchlorazole, fenchlorazole-ethyl, fenclorim, flurazole, fluxofenim, furilazole, harpin proteins, isoxadifen-ethyl, jiecaowan, jiecaoxi, mefenpyr, mefenpyr-diethyl, mephenate, naphthalic anhydride, 2,2,5-trimethyl-3-(dichloroacetyl)-1,3-oxazolidine, 4-(dichloroacetyl)-1-oxa-4-azaspiro[4.5]decane, oxabetrinil, 829148, and N-phenyl-sulfonylbenzoic acid amides, as well as agriculturally acceptable salts and esters thereof, provided they have a carboxyl group. In some embodiments, the safener can be cloquintocet or an ester or salt thereof, such as cloquintocet (mexyl).

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivatives, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamine B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like or less, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like or less, esters of the above vegetable oils or less, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like or less, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof. Exemplary solid carriers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

In some embodiments, emulsions, pastes or oil dispersions, can be prepared by homogenizing (a) and/or (b) in water by means of wetting agent, tackifier, dispersant or emulsifier. In some embodiments, concentrates suitable for dilution with water are prepared, comprising (a), optionally (b), a wetting agent, a tackifier, and a dispersant or emulsifier.

In some embodiments, powders or materials for spreading and dusts can be prepared by mixing or concomitant grinding of (a) and/or (b) and optionally a safener with a solid carrier.

In some embodiments, granules (e.g., coated granules, impregnated granules and homogeneous granules) can be prepared by binding the (a) and (b) to solid carriers.

The concentration of (a) and when present, the concentration of (b), in the formulation can be varied. In some embodiments, the formulations comprise from 1% to 95% (e.g., from 5% to 95%, from 10% to 80%, from 20% to 70%, from 30% to 50%) by total weight of (a) and (b), when present. In some embodiments, (a) and when present, (b), independently, can be employed in a purity of from 90% to 100% (e.g., from 95% to 100%) according to NMR spectrometry. In some embodiments, the concentration of (a), and when present, the concentration of (b) and the concentration of additional pesticides, in the formulations can be varied. In some embodiments, the formulations comprise from 1% to 95% (e.g., from 5% to 95%, from 10% to 80%, from 20% to 70%, from 30% to 50%) by total weight of (a), and when present, (b) and additional pesticides. In some embodiments, (a), and when present, (b) and additional pesticides, independently, can be employed in a purity of from 90% to 100% (e.g., from 95% to 100%) according to NMR spectrometry.

Methods of Application

The formulations described above containing (a) and/or (b) can be applied by any known technique for applying herbicides. Exemplary application techniques include, but are not limited to, spraying, atomizing, dusting, spreading, or direct application. The method of application can vary depending on the intended purpose. In some embodiments, the method of application can be chosen to ensure the finest possible distribution of the compositions disclosed herein.

The formulations disclosed herein can be applied pre-emergence (before the emergence of undesirable vegetation) or post-emergence (i.e., during and/or after emergence of the undesirable vegetation). In some cases, the formulations are applied to the undesirable vegetation when the undesirable vegetation has reached the 1-10 leaf stage (e.g., when the undesirable vegetation has reached the 1-6 leaf stage).

Formulations containing (a) and/or (b) can be applied after seeding or transplanting and before or after the emergence of the chicory plants and/or the undesirable vegetation. In some embodiments, the formulations show good crop tolerance (e.g., little to no phytotoxicity) even when the chicory is actively growing. Accordingly, the formulations can be applied during or after the emergence of the chicory plants to control undesirable vegetation.

In some embodiments, the formulations disclosed herein containing (a) and/or (b) are applied to chicory vegetation or an area adjacent the vegetation or applied to soil to prevent the emergence or growth of vegetation by spraying (e.g., foliar spraying). In some embodiments, the spraying techniques use, for example, water as carrier and spray liquor rates of from 2 liters per hectare (L/ha) to 2000 L/ha (e.g., from 10 L/ha to 1000 L/ha, or from 50 to 500 L/ha). In some embodiments, the formulations disclosed herein are applied by the low-volume or the ultra-low-volume method, wherein the application is in the form of micro granules. In some embodiments, wherein the formulations disclosed herein are less well tolerated by certain chicory plants, the formulations can be applied with the aid of the spray apparatus in such a way that they come into little contact, if any, with the leaves of the sensitive chicory plants while reaching the leaves of undesirable vegetation that grows underneath or on the bare soil (e.g., post-directed or lay-by).

In some embodiments, herbicidal activity is exhibited by (a) and optionally (b) when they are applied directly to the plant or to the locus of the plant at any stage of growth or before planting, emergence, or during plant growth up to harvest. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action.

The methods disclosed herein can be used to control undesired vegetation in chicory without significant crop damage. The methods disclosed herein can be used in chicory crops that are resistant to, for instance, herbicides, pathogens, and/or insects. In some embodiments, the methods disclosed herein can be used in chicory plants that are resistant to one or more herbicides because of genetic engineering or breeding. For example, in some embodiments, the undesirable vegetation can be controlled in glyphosate-, 5-enolpyruvylshikimate-3-phosphate (EPSP) synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase (ACCase) inhibitor-, imidazolinone-, sulfonylurea-, pyrimidinylthiobenzoate-, triazolopyrimidine-sulfonamide-, sulfonylaminocarbonyltriazolinone-, acetolactate synthase (ALS) or acetohydroxy acid synthase (AHAS) inhibitor-, 4-hydroxyphenyl-pyruvate dioxygenase (HPPD) inhibitor-, phytoene desaturase inhibitor-, carotenoid biosynthesis inhibitor-, protoporphyrinogen oxidase (PPO) inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, triazine-, or bromoxynil-tolerant chicory crops. In certain embodiments, the chicory crop can possesses multiple or stacked traits conferring tolerance to multiple herbicides or multiple modes-of-action. In some embodiments, the methods disclosed herein can be used in chicory plants that are resistant to one or more pathogens such as plant pathogenous fungi owing to genetic engineering or breeding. In some embodiments, the methods disclosed herein can be used in chicory plants that are resistant to attack by insects owing to genetic engineering or breeding. In certain embodiments, the chicory is not genetically engineered or bred to exhibit herbicide resistance (e.g., to exhibit resistance to an ALS inhibitor).

In some embodiments, the compositions disclosed herein can be used for controlling broadleaf weeds, grass weeds, sedge weeds, and combinations thereof. In some cases, the undesirable vegetation is selected from *Artemisia biennis* (ARTBI; biennial wormwood), *Capsella bursa-pastoris* (CAPBP; shepherd's purse), *Coronopus didymus* (COPDI; lesser swinecress), *Galinsoga ciliate* (GASCI; shaggy soldier), *Galinsoga parviflora* (GASPA; potato weed), *Matricaria chamomilla* (MATCH; wild chamomile), *Senecio vulgaris* (SENVU; common groundsel), *Solanum nigrum* (SOLNI; black nightshade), *Sonchus* species (SONSS) such as spiny sow thistle, field or perennial sow thistle, common sow thistle, marsh sow thistle, and milk thistle; and combinations thereof.

The undesirable vegetation can comprise a herbicide resistant or tolerant weed. For example, the resistant or tolerant weed can be a biotype resistant or tolerant to acetolactate synthase (ALS) or acetohydroxy acid synthase (AHAS) inhibitors, photosystem II inhibitors, acetyl CoA carboxylase (ACCase) inhibitors, synthetic auxins, auxin transport inhibitors, photosystem I inhibitors, 5-enolpyruvylshikimate-3-phosphate (EPSP) synthase inhibitors, microtubule assembly inhibitors, fatty acid and lipid biosynthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, and herbicides with multiple modes-of-action. The herbicide resistant or tolerant weed can also comprise a biotype with resistance or tolerance to multiple herbicides, multiple chemical classes, multiple herbicide modes-of-action or via multiple resistance mechanisms.

By way of non-limiting illustration, examples of certain embodiments of the present disclosure are given below.

EXAMPLES

Field trials were conducted in Northern France and Belgium, both of which are major areas for root chicory and whitloof chicory production. Trials were conducted in accordance with EPPO standard PP 1/99(3) entitled "Weeds in Roots Vegetables," PP 1/152(4) entitled "Design and Analysis of Efficacy Evaluation Trials," PP 1/135(3) entitled "Phytotoxic Assessment," and PP 1/181(4) entitled "Conduct and Reporting of Efficacy Evaluation Trials Including Good Experimental Practice," all of which are incorporated herein by reference in their entirety.

Application to all field trials was made using a small plot precision sprayer operating at between 160-400 kilopascals (kPa) pressure, delivering a spray volume of 150-400 liters per hectare (L/ha). Nozzles were of a flat fan type. Trial plot size ranged from 4.5×2.5 square meters ($m^2$) to 10.5×2.5 $m^2$. Plots were replicated 3 or 4 times and were arranged in a randomized block design within each trial. All trials received a pre-emergence application of BONALAN® at 6 L/ha (benfluralin; 180 grams active ingredient per liter (g ai/L); commercially available from Dow AgroSciences LLC) with incorporation to prevent the emergence of grasses which could complicate the assessment of broadleaf control.

In whitloof chicory (*Cichorium intybus*), treatments were evaluated which included either two or three post-emergence applications of herbicide. Multiple applications of herbicide were evaluated for their ability to control weed emergence during the extended period of time required for chicory cultivation. Trials included different combinations of application rate and application timing. Broadcast applications were made from May to July, covering a range of possible application timings. Penoxulam was applied at a maximum total rate of 15 g/ha per season, applied in two or three applications with a minimum of seven days between applications. Treatment with penoxsulam involved application of either BOA® or VIPER® (2.14% weight per weight (w/w) oil dispersions of penoxsulam commercially available from Dow AgroSciences LLC). Trials were also conducted using another ALS mode-of-action herbicide (i.e., the sulfonylurea triflusulfuron-methyl). Triflusulfuron-methyl was applied at a maximum total rate of 30 g/ha per season, applied in two or three applications with a minimum of seven days between applications. Treatment with triflusulfuron-methyl involved application of SAFARI® (triflusulfuron-methyl; commercially available from DuPont Crop Protection).

Prior to treatment application, assessments of weed populations (number of plants per $m^2$) were carried out using a quadrant square and an appropriate number of sampling points.

Three different methods were used to evaluate the effectiveness of treatments for the control of undesirable vegetation:

1) Visual rating in percent of the overall volume reduction of vegetation for each species compared to the nearest untreated plot (Plant/Control/% visual; 0%=no control; 100%=all weeds dead). Assessments of this type were performed by Dow AgroSciences LLC in France.

2) Counts were made of number of weed plants per $m^2$ or by plot (Plant/count/number/$m^2$, linear m or plot). These counts were performed by the French (APEF) and Belgian Institutes.

3) Following treatments, the remaining plants were weighed to determine the mass per plant (expressed as g/plant) one month after the last pesticide application. These assessments were performed by the APEF.

Assessments of weed control were carried out at 14, 28, 56 and 84 days or longer after each application timing (DAAA=days after application A, DAAB=days after application B or DAAC=days after application C).

The results of the weed control trials are summarized in Table 1. Tables 2-5 provide chicory plant evaluation results for leaf and root measurements. Unexpectedly, penoxsulam provided good control of undesirable vegetation when applied post-emergence to the crop and weeds with commercially acceptable crop tolerance. While treatment with penoxsulam did result in some visible crop injury, no deleterious effect on root yield was observed.

TABLE 1

Percent weed control (0-100 scale) at 30 days after the conclusion of two or three post-emergence applications of penoxsulam or SAFARI ® (triflusulfuron-methyl) to chicory.

| | 2 applications | | | 3 applications | | |
|---|---|---|---|---|---|---|
| | Rate (g ai/ha)/timing | | | | | |
| | Penoxsulam (g ai/ha) | | SAFARI ® (g ai/ha) | Penoxsulam (g ai/ha) | | SAFARI ® (g ai/ha) |
| | 5.6/5.6 | 7.5/7.5 | 15/15 | 3.73/3.73/3.73 | 5/5/5 | 10/10/10 |
| | | | % Visual Weed Control* | | | |
| COPDI (2 trials) | 92.4 | 96.25 | 16.65 | 90.15 | 93.25 | 36.65 |
| GASCI-GASPA (4 trials) | 87.3 | 87.9 | 31.7 | 95.9 | 96.7 | 55.9 |
| CAPBP (2 trials) | 100 | 100 | 25 | 100 | 100 | 12.5 |
| MATCH (2-3 trials) | 93 (2) | 93.9 (3) | 69.4 (3) | 91.4 (2) | 97.2 (3) | 89.8 (3) |
| ARTRI (3 trials) | 64.4 | 68.3 | 30.3 | 68.8 | 76.4 | 48 |
| SQLNI (2 trials) | 66.5 | 100 | 6.5 | 83.4 | 83.4 | 23.5 |

TABLE 1-continued

Percent weed control (0-100 scale) at 30 days after the conclusion of two or three post-emergence applications of penoxsulam or SAFARI ® (triflusulfuron-methyl) to chicory.

| | 2 applications | | | 3 applications | | |
|---|---|---|---|---|---|---|
| | Rate (g ai/ha)/timing | | | | | |
| | Penoxsulam (g ai/ha) | | SAFARI ® (g ai/ha) | Penoxsulam (g ai/ha) | | SAFARI ® (g ai/ha) |
| | 5.6/5.6 | 7.5/7.5 | 15/15 | 3.73/3.73/3.73 | 5/5/5 | 10/10/10 |
| | % Visual Weed Control* | | | | | |
| SENVU (1 trial) | 50 | 100 | 100 | 60 | 100 | 80 |
| SONSS (1 trial) | 86 | 86 | 57 | 86 | 86 | 57 |

*Percent Weed Control = 0-100 scale, where 0 = no control and 100 complete control.
g ai/ha = grams active ingredient per hectare
COPDI = *Coronopus didymus* (lesser swinecress)
GASCI = *Galinsoga ciliata* (shaggy soldier)
GASPA = *Galinsoga parviflora* (potato weed)
CAPBP = *Capsella bursa-pastoris* (shepherd's purse)
MATCH = *Matricaria recutita* (wild chamomile)
ARTBI = *Artemisia biennis* (biennial wormwood)
SOLNI = *Solanum nigrum* (black nightshade)
SENVU = *Senecio vulgaris* (common groundsel)
SONSS = *Sonchus* sp. (sow-thistle)

TABLE 2

Effect of post-emergence applications of penoxsulam or SAFARI ® (triflusulfuron-methyl) on chicory leaf development in two different varieties of chicory.

| Treatment Rate | | Average number of leaves (measured 21 DAAC) | | | Average number of leaves (measured 31 DAAC) | | |
|---|---|---|---|---|---|---|---|
| (g ai/ha)/Timing | | Ecrine | Hermès | Average | Ecrine | Hermès | Average |
| Penoxsulam | 7.5/7.5 | 7 | 6 | 7 a | 14 | 14 | 14 b |
| | 15/15 | 8 | 6 | 7 a | 14 | 14 | 14 b |
| | 11.2/11.2 | 7 | 7 | 7 a | 13 | 15 | 14 b |
| SAFARI ® | 15/15 | 8 | 8 | 8 a | 16 | 16 | 16 a |
| | 22.5/22.5 | 9 | 8 | 8 a | 15 | 17 | 16 a |
| | 30/30 | 8 | 8 | 8 a | 15 | 17 | 16 a |
| Penoxsulam | 5/5/5 | 7 | 7 | 7 a | 14 | 16 | 15 ab |
| | 10/10/10 | 8 | 7 | 7 a | 15 | 15 | 15 ab |
| SAFARI ® | 7.5/7.5/7.5 | 8 | 7 | 7 a | 15 | 15 | 15 ab |
| | 10/10/10 | 8 | 8 | 8 a | 15 | 17 | 16 a |
| | 20/20/20 | 8 | 8 | 8 a | 15 | 17 | 16 a |
| | 15/15/15 | 8 | 8 | 8 a | 15 | 17 | 16 a |
| Untreated | | 8 | 8 | 8 a | 15 | 17 | 16 a |
| Average | | 8 | 7 | 8 | 15 b | 16 a | 15 |
| Anova "variety"[†] | | | NS | | | THS | |
| Anova "treatment"[†] | | | S | | | THS | |

[†]Comparison of averages using the Newman-Keuls method (5%). The letters following each average indicate a statistically significant difference between averages, as determined by Newman-Keuls analysis (5% level). Two averages labeled with different letters are statistically different, as determined by Newman-Keuls analysis.

TABLE 3

Effect of post-emergence applications of penoxsulam or SAFARI ® (triflusulfuron-methyl) on chicory root development in two different varieties of chicory.

| Treatment Rate | | Number of roots/10 m$^2$ (measured 129 DAAC) | | Number of roots/10 m$^2$ (measured 149 DAAC) | | Number of roots for forcing/10 m$^2$ (measured at uprooting) | |
|---|---|---|---|---|---|---|---|
| (g ai/ha)/Timing | | Ecrine | Hermès | Ecrine | Hermès | Ecrine | Hermès |
| Penoxsulam | 7.5/7.5 | 288 | 170 | 288 | 184 | 230 | 155 |
| | 15/15 | 253 | 177 | 247 | 160 | 219 | 135 |
| | 11.2/11.2 | 267 | 194 | 285 | 208 | 245 | 162 |
| SAFARI ® | 15/15 | 236 | 188 | 250 | 194 | 244 | 147 |
| | 22.5/22.5 | 274 | 174 | 267 | 167 | 260 | 177 |
| | 30/30 | 267 | 153 | 264 | 146 | 244 | 164 |

TABLE 3-continued

Effect of post-emergence applications of penoxsulam or SAFARI ® (triflusulfuron-methyl) on chicory root development in two different varieties of chicory.

| Treatment Rate (g ai/ha)/Timing | | Number of roots/10 m² (measured 129 DAAC) | | Number of roots/10 m² (measured 149 DAAC) | | Number of roots for forcing/10 m² (measured at uprooting) | |
|---|---|---|---|---|---|---|---|
| | | Ecrine | Hermès | Ecrine | Hermès | Ecrine | Hermès |
| Penoxsulam | 5/5/5 | 253 | 198 | 271 | 181 | 233 | 146 |
| | 10/10/10 | 267 | 191 | 257 | 181 | 227 | 157 |
| | 7.5/7.5/7.5 | 264 | 205 | 250 | 194 | 238 | 153 |
| SAFARI ® | 10/10/10 | 274 | 181 | 285 | 160 | 248 | 182 |
| | 20/20/20 | 260 | 198 | 250 | 201 | 242 | 153 |
| | 15/15/15 | 260 | 188 | 292 | 181 | 251 | 161 |
| Untreated | | 248 | 170 | 247 | 137 | 245 | 159 |
| Average | | 262 a | 183 b | 264 a | 173 b | 241 a | 158 b |
| Overall average | | 222 | | 218 | | 199 | |
| Standard deviation | | 34 | | 37 | | 24 | |
| CV | | 15 | | 17 | | 12 | |
| Anova "variety"† | | THS | | THS | | THS | |
| LSD | | 12.90 | | 13.94 | | 9.08 | |
| Anova "treatment"† | | NS | NS | NS | NS | NS | NS |

†Comparison of averages using the Newman-Keuls method (5%). The letters following each average indicate a statistically significant difference between averages, as determined by Newman-Keuls analysis (5% level). Two averages labeled with different letters are statistically different, as determined by Newman-Keuls analysis.

TABLE 4

Effect of post-emergence applications of penoxsulam or SAFARI ® (triflusulfuron-methyl) on the number of roots suitable for forcing in two different varieties of chicory.

| Treatment Rate (g ai/ha)/Timing | | % Roots for forcing (measured 129 DAAC) | | Average weight of roots for forcing | |
|---|---|---|---|---|---|
| | | Ecrine | Hermès | Ecrine | Hermès |
| Penoxsulam | 7.5/7.5 | 97 | 96 | 198 | 255 |
| | 15/15 | 96 | 99 | 211 | 264 |
| | 11.2/11.2 | 97 | 97 | 192 | 237 |
| SAFARI ® | 15/15 | 98 | 96 | 198 | 263 |
| | 22.5/22.5 | 97 | 96 | 198 | 245 |
| | 30/30 | 95 | 97 | 195 | 246 |
| Penoxsulam | 5/5/5 | 98 | 96 | 199 | 250 |
| | 10/10/10 | 98 | 99 | 202 | 271 |
| | 7.5/7.5/7.5 | 99 | 98 | 201 | 255 |
| SAFARI ® | 10/10/10 | 96 | 97 | 202 | 239 |
| | 20/20/20 | 98 | 100 | 206 | 276 |
| | 15/15/15 | 99 | 97 | 202 | 269 |
| Untreated | | 96 | 98 | 201 | 252 |
| Average | | 97 | 97 | 200 | 255 |
| Overall average | | 97 | | 228 | |
| Standard deviation | | 2 | | 19 | |
| CV | | 6(1) | | 9 | |
| Anova "variety"† | | NS | | THS | |
| LSD | | — | | 7.294 | |
| Anova "treatment"† | | NS | NS | NS | NS |

†Analysis and comparison of averages on arcsin√p (p = % of roots for forcing)

Trials were also performed to investigate the effect of post-emergence applications of penoxsulam or SAFARI® (triflusulfuron-methyl) on the yield of chicons in two different varieties of chicory. The trial was carried out on plots measuring 3×5 meters. Two varieties of chicory (Hermes and Ecrine) were sown. Treatments were carried out, as described above (a) 18 days after sowing, (b) 25 days after sowing, and (c) 32 days after sowing. Trial assessments were carried out 21 DAAC and 46 DAAC on the number of plants per linear meter, and on their development stage (number of leaves per plant).

Harvest was carried out 171 DAAC on 4 rows per plot. After harvest, the roots were counted and weighted, and the percent of roots usable for forcing was measured. The roots were then stored in a conservation room for 21 days until start of forcing phase. After 21 days of forcing, the chicons produced were weighed and classified in the commercial quality categories. The brut yield (total weight of chicons produced; marketable+non-marketable), net yield (weight of marketable chicons produced) and best class yield (Extra+1=weight of Extra and First Class chicons produced) were measured (in kilograms per 10 square meters (kg/10 m²)). The results of these trials are summarized in Table 5.

TABLE 5

Effect of post-emergence applications of penoxsulam or SAFARI ® (triflusulfuron-methyl) on the yield of chicons in two different varieties of chicory.

| Treatment Rate (g ai/ha)/Timing | | Yield of Chicons in Kg/10 m² of Field (measured 171 DAAC and 21 days after the start of forcing) | | | | | | |
|---|---|---|---|---|---|---|---|---|
| | | Brut[1] | | | Net[2] | | Extra + 1[3] | |
| | | Ecrine | Hermès | Average | Ecrine | Hermès | Ecrine | Hermès |
| Penoxsulam | 7.5/7.5 | 42.4 | 36.7 | 39.6 | 33.9 | 26.6 | 28.2 | 21.1 |
| | 15/15 | 46.4 | 33.4 | 39.9 | 37.4 | 22.5 | 30.7 | 16.1 |
| | 11.2/11.2 | 42.8 | 37 | 39.9 | 33.2 | 28.6 | 25 | 22.8 |

TABLE 5-continued

Effect of post-emergence applications of penoxsulam or SAFARI ® (triflusulfuron-methyl) on the yield of chicons in two different varieties of chicory.

| Treatment Rate (g ai/ha)/Timing | | Yield of Chicons in Kg/10 m² of Field (measured 171 DAAC and 21 days after the start of forcing) | | | | | | |
|---|---|---|---|---|---|---|---|---|
| | | Brut[1] | | | Net[2] | | Extra + 1[3] | |
| | | Ecrine | Hermès | Average | Ecrine | Hermès | Ecrine | Hermès |
| SAFARI ® | 15/15 | 45.5 | 34.5 | 40.0 | 38.7 | 23.8 | 31 | 16.7 |
| | 22.5/22.5 | 48 | 40.8 | 44.4 | 36.3 | 30.7 | 26.4 | 24.5 |
| | 30/30 | 47.1 | 37.6 | 42.4 | 36.1 | 26.8 | 27.3 | 19.7 |
| Penoxsulam | 5/5/5 | 47.5 | 33.8 | 40.7 | 36.4 | 25.6 | 29 | 17.7 |
| | 10/10/10 | 50.7 | 39.4 | 45.1 | 38.7 | 27.7 | 29.5 | 19.2 |
| | 7.5/7.5/7.5 | 45.1 | 36.5 | 40.8 | 34.6 | 25.7 | 27.2 | 18.6 |
| SAFARI ® | 10/10/10 | 50 | 42.2 | 46.1 | 38.1 | 30.5 | 29.9 | 21.3 |
| | 20/20/20 | 48.7 | 38.9 | 43.8 | 37.1 | 26.7 | 26 | 19.4 |
| | 15/15/15 | 52 | 41.5 | 46.8 | 39.4 | 29.9 | 29.8 | 20.7 |
| Untreated | | 48.5 | 34.6 | 41.6 | 36.5 | 24.8 | 27.8 | 18.3 |
| Average | | 47.4 a | 37.3 b | | 36.6 a | 26.6 b | 28.3 a | 19.6 b |
| Overall average | | | | 42.3 | | 31.7 | | 23.9 |
| Standard deviation | | | | 4.6 | | 4.3 | | 4.0 |
| CV | | | | 18.0 | | 13.4 | | 16.9 |
| Anova "variety" | | | | THS | | THS | | THS |
| LSD | | | | 1.729 | | 1.598 | | 1.521 |
| Anova "treatment" | | | | S | | NS | | NS |
| LSD | | | | 7.952 | | — | | — |

[1]Brut = total weight of chicons produced (marketable + non-marketable chicons)
[2]Net = weight of marketable chicons produced
[3]Extra + 1 = weight of Extra and First Class chicons produced The methods of the appended claims are not limited in scope by the specific methods described herein, which are intended as illustrations of a few aspects of the claims and any methods that are functionally equivalent are intended to fall within the scope of the claims. Various modifications of the methods in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method of controlling undesirable vegetation in chicory comprising applying to the vegetation or an area adjacent the vegetation, or applying to the soil adjacent thereto, a herbicidally effective amount of (a) penoxsulam or an agriculturally acceptable salt thereof, wherein the vegetation is present or will be present in chicory.

2. The method of claim 1, wherein (b) a second pesticide or an agriculturally acceptable salt or ester thereof is applied to the vegetation or the area adjacent the vegetation, or to the soil adjacent thereto.

3. The method of claim 2, wherein (a) and (b) are applied simultaneously.

4. The method of claim 2, wherein (b) includes an acetolactate synthase (ALS) inhibitor, an inhibitor of microtubule assembly, a cellulose biosynthesis inhibitor, a protoporphyrinogen oxidase (PPO) inhibitor, or combinations thereof.

5. The method of claim 4, wherein (b) is selected from the group consisting of triflusulfuron-methyl, propyzamide, benfluralin, trifluralin, isoxaben, flumioxazin, and combinations thereof.

6. The method of claim 2, wherein (b) is applied in an amount of from 20 to 1200 g ai/ha.

7. The method of claim 2, wherein (a) and (b) are applied in a weight ratio of (a) to (b) from 1:500 to 1:2.

8. The method of claim 1, wherein the chicory comprises *Cichorium intybus* L. var. *sativum*.

9. The method of claim 1, wherein the chicory comprises *Cichorium intybus* L. var. *foliosum*.

10. The method of claim 1, wherein (a) is applied after emergence of the undesired vegetation.

11. The method of claim 1, wherein (a) is applied prior to emergence of the undesired vegetation.

12. The method of claim 2, wherein (b) is applied prior to emergence of the undesired vegetation, and (a) is applied after emergence of the undesired vegetation.

13. The method of claim 1, wherein the undesirable vegetation includes *Artemisia biennis, Capsella bursa-pastoris, Coronopus didymus, Galinsoga ciliata, Galinsoga parviflora, Matricaria chamomilla, Senecio vulgaris, Solanum nigrum, Sonchus* species, and combinations thereof.

14. The method of claim 1, wherein (a) is applied in an amount of from 3 to 15 g ai/ha.

15. The method of claim 1, further comprising applying a herbicide safener.

16. The method of claim 1, further comprising applying an agriculturally acceptable adjuvant or carrier.

17. The method of claim 1, wherein the chicory is not genetically engineered or bred to exhibit herbicide resistance.

18. The method of claim 1, wherein the chicory is not genetically engineered or bred to exhibit resistance to an ALS inhibitor.

19. The method of claim 1, wherein the chicory possesses single, multiple or stacked traits conferring tolerance to single or multiple herbicides or single or multiple modes-of-action.

20. The method of claim 1, wherein the undesirable vegetation comprises a herbicide resistant or tolerant weed.

21. The method of claim 2, wherein (b) is applied after emergence of the undesired vegetation.

22. The method of claim 2, wherein (b) is applied prior to emergence of the undesired vegetation.

* * * * *